United States Patent [19]
McGhee et al.

[11] Patent Number: 5,302,717
[45] Date of Patent: Apr. 12, 1994

[54] PREPARATION OF URETHANE AND CARBONATE PRODUCTS

[75] Inventors: William D. McGhee, St. Louis; John J. Talley, Chesterfield, both of Mo.

[73] Assignee: Monsanto Company, St. Louis, Mo.

[21] Appl. No.: 961,734

[22] Filed: Oct. 15, 1992

[51] Int. Cl.$^5$ .................... C07D 211/16; C07C 68/04
[52] U.S. Cl. .................................. 546/226; 558/275; 560/115
[58] Field of Search ........................ 546/226; 558/275; 560/115

[56] References Cited

U.S. PATENT DOCUMENTS

| 4,467,089 | 8/1984 | Bechara | 544/351 |
| 5,200,547 | 4/1993 | Riley et al. | 558/265 |

FOREIGN PATENT DOCUMENTS

| 0477159A1 | 3/1992 | European Pat. Off. |
| 56-002937 | 1/1981 | Japan. |
| 57-058645 | 4/1982 | Japan. |

OTHER PUBLICATIONS

Grant, R., Grant & Hackh's Chemical Dictionary, fifth edition, 1987, p. 444.

Aresta, M. and Quaranta, E., "Role of the Macrocyclic Polyether in the Synthesis of N-Alkylcarbamate Esters from Primary Amines, CO$_2$ and Alkyl Halides in the Presence of Crown-Ethers", *Tetrahedron*, 48, 1515-30 (1992).

Yoshida, Y. et al., "Novel Synthesis of Carbamate Ester from Carbon Dioxide, Amines, and Alkyl Halides", *Bull. Chem. Soc. Jpn.*, 62, 1534-38 (1989).

Hori, Y. et al., "New Organic Synthesis with DBU: Part 7. Synthesis of Carbonates and Carbamates with Carbon Dioxide Gas as the Starting Material", *Chemistry Express*, vol. 1, No. 4, pp. 224-227 (1986).

Schwesinger, R. and Schlemper, H., "Peralkylated Polyaminophosphazenes—Extremely Strong, Neutral Nitrogen Bases", *Angew. Chem. Int. Ed. Engl.*, 26, 11, pp. 1167-1169 (1987).

Schwesinger, R. "Extremely Strong, Non-ionic Bases: Synthesis and Applications", *Chimia*, 39, 9, pp. 269-272 (1985).

Primary Examiner—Mary C. Lee
Assistant Examiner—Jacqueline Haley
Attorney, Agent, or Firm—Kenneth D. Goetz; Paul L. Passley; James C. Bolding

[57] ABSTRACT

The present invention provides a process for preparing urethanes and carbonates from an amine or an alcohol, carbon dioxide and a hydrocarbyl halide. The amine or alcohol is reacted with carbon dioxide in a suitable solvent system and in the presence of a base selected from the group consisting of a phosphazene compound and a mixture of a phosphazene compound and an organic, nitrogenous base, to form the ammonium carbamate or carbonate salt which is then reacted in a polar aprotic solvent with a hydrocarbyl halide. Polymer products can also be prepared utilizing this process or utilizing the resulting urethanes and carbonates under standard polymerization conditions.

11 Claims, No Drawings

PREPARATION OF URETHANE AND CARBONATE PRODUCTS

BACKGROUND OF THE INVENTION

1. Field of the Invention

The present invention relates to a process for preparing urethanes and carbonates and, more particularly, relates to a new and useful process for preparing urethanes from amines, carbon dioxide and a hydrocarbyl halide and for preparing carbonates from alcohols, carbon dioxide and a hydrocarbyl halide. The present invention also relates to polymers prepared from such urethanes and/or carbonates.

2. Prior Art

Urethanes and carbonates are typically synthesized by the reaction of a primary amine or an alcohol with phosgene to form an isocyanate or carbonate salt. Thereafter, the isocyanate or carbonate is reacted with an alcohol to form the corresponding urethane or carbonate. Phosgene is very toxic and thus requires very careful handling from a product and worker safety standpoint. Isocyanates are sensitizers and are extremely toxic as well. Preparing urethane and carbonate products without using phosgene and in an economical manner, and preparing urethane products without generating isocyanates would be an achievement of considerable significance in the art.

U.S. Pat. No. 4,467,089 discloses the preparation of certain carbamic acid derivatives (carbonates and carbamate esters) by the simultaneous reaction of a secondary amine and a tertiary amine with carbon dioxide to produce corresponding tertiary amine salts of N-substituted carbamic acid. The secondary and tertiary amines are brought together in equimolar proportions in the presence of excess carbon dioxide under mild conditions. The secondary amine reacts with $CO_2$ in the presence of the tertiary amine to form the corresponding disubstituted tertiary ammonium carbamate salt. The salt is described as being useful as heat activatable delayed action catalysts, especially for use in polyurethane formulations.

Yoshida et al, Bull. Chem. Soc. Jpn., 62, 1534-38 (1989) discloses preparation of urethanes from amines, carbon dioxide and alkyl halides. However, under the reaction conditions specified therein, yields of urethane product are poor as nitrogen derived products are the predominant product.

In Chemistry Express, Vol. 1, No. 4, pp 224-227 (1986), Kinki Chemical Society, Japan, it is disclosed that primary and secondary amines absorb $CO_2$ to form carbamic acid amine salts and that when an equivalent of 1,8-diazabicyclo[5.4.0]undec-7-ene (DBU) is added, additional $CO_2$ is absorbed to form the DBU-carbamate salt. The DBU-carbamate salt when reacted in a nonpolar aprotic solvent with an alkylating agent forms a carbamate ester (urethane). Yield and selectivity of the urethane product are highly dependent on the nature of the alkylating agent. When dibutylamine is reacted with $CO_2$ in the presence of DBU and the resulting DBU-carbamate salt is reacted with butyl chloride as the alkylating agent, a yield of only 17% is realized. With butyl bromide, the yield is 86%. However, when the reaction with butyl bromide was repeated, it was observed that this yield could be achieved only if the reaction was allowed to continue for an extensive period of time, such as from about 18 to about 30 hours. Thus, this reaction, like the reaction disclosed by Yoshida et al, is not commercially practicable.

It has now been discovered that unexpectedly high yields can be achieved in a commercially practicable period of time, i.e. from one-fourth to one-half of the time set forth above, by conducting the reaction in a polar aprotic solvent and in the presence of a base selected from a phosphazene compound or a mixture of a phosphazene compound and an organic, nitrogenous base.

SUMMARY OF THE INVENTION

The present invention provides a new and useful process for making urethanes and carbonates. The present invention also provides a new and useful process for making polyurethanes and polycarbonates. A preferred embodiment of the present inventive process is a process for making urethanes and carbonates of the following general formula:

wherein $R_1$ represents alkyl, alkenyl, cycloalkyl, cycloalkenyl, aralkyl, and aralkenyl radicals having from 1 to about 22 carbon atoms; A represents a radical selected from the group consisting of $-NR'_2R'_3$, $NHCH(R''_3)COOR_1$ and $OR_4$ wherein R, $R'_2$, $R'_3$ and $R''_3$ independently represent hydrogen and alkyl, alkenyl, cycloalkyl, cycloalkenyl, aryl, aralkyl, aralkenyl, alkenaryl and alkaryl radicals having from 1 to about 22 carbon atoms, provided that not more than one of $R'_2$ and $R'_3$ in the formula $-NR'_2R'_3$ is hydrogen; and $R_4$ represents alkyl, alkenyl, cycloalkyl, cycloalkenyl, aralkyl, aralkenyl, alkenaryl, and alkaryl radicals having from 1 to about 22 carbon atoms.

$R'_2$ and $R'_3$ together with the nitrogen may be bound to form a saturated or unsaturated heterocyclic 5 to 9 membered ring radical, such as morpholino, pyrrolidino, piperidino, and the like. In addition, one of $R'_2$ or $R'_3$ can be

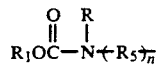

wherein n represents an integer of from 0 to about 8; R is as defined above, R is as defined above and $R_5$ represents alkylene radicals, which may be straight-chain or branched, having from 1 to about 22 carbon atoms, i.e., the new and novel urethanes of this invention may be diurethanes. Likewise, $R_4$ can be

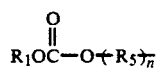

wherein n represents an integer of from 0 to about 8; $R_1$ and $R_2$ are as defined above, and $R_5$ represents alkylene radicals, which may be straight chain or branched, having from 1 to about 22 carbon atoms, i.e., the new and novel carbonates may be dicarbonates.

The process for preparing the subject urethanes and carbonates is characterized by reacting, in the presence of a base selected from the group consisting of a phosphazene compound and a mixture of a phosphazene compound and an organic, nitrogenous base selected from the group consisting of guanidine compounds, amidine compounds and mixtures thereof, a suitable primary or secondary mono- or polyamine, or a suitable primary, secondary or tertiary mono-alcohol or polyol, with carbon dioxide to form the corresponding carbamate salt or carbonate salt which is then reacted with a hydrocarbyl halide. In order to achieve high yields in a reasonable period of time, the reaction between the salt and the hydrocarbyl halide is carried out in a polar aprotic solvent. Although the reaction between the amine or alcohol and carbon dioxide can be conducted in a variety of solvents, it is preferred to conduct such reaction in the polar aprotic solvent as well, primarily for convenience to avoid isolation of the salt.

The present invention is based on nucleophilic attack on the hydrocarbyl halide by carbamate anions pre-made from $CO_2$, a primary or secondary mono- or polyamine and a tertiary amine base, or by nucleophilic attack of carbonate anions pre-made from $CO_2$, a primary, secondary or tertiary mono-alcohol or polyol and a tertiary amine base. Urethane products made in accordance with the present invention are useful in specialty chemical applications, such as, for example, as cross-linking agents. Carbonate products made in accordance with this invention are useful in preparing polymers which are useful in shatter-resistant optical lenses, face shields and windows.

DETAILED DESCRIPTION OF THE INVENTION

The urethanes are prepared in accordance with the present invention by bringing into reactive contact a suitable primary or secondary mono- or diamine, or a mixture thereof, carbon dioxide and a base selected from the group consisting of a phosphazene compound and a mixture of a phosphazene compound and an organic, nitrogenous base selected from the group consisting of guanidine compounds, amidine compounds and mixtures thereof, in a confined zone, such as a reactor, to prepare the corresponding ammonium carbamate salt. Similarly, the carbonates are prepared in accordance with the present invention by bringing into reactive contact a suitable primary, secondary or tertiary monoalcohol or diol, or polyol or a mixture thereof, carbon dioxide and a base selected from the group consisting of a phosphazene compound and a mixture of a phosphazene compound and an organic, nitrogenous base selected from the group consisting of guanidine compounds, amidine compounds and mixtures thereof in a confined zone, such as a reactor, to prepare the corresponding carbonate salt. Preferably the amines or alcohols are in solution and the carbon dioxide is bubbled through the solution. The reaction proceeds without the need of elevated pressure or temperatures in a slightly exothermic reaction to give either the ammonium salt of the corresponding carbamate anion or the salt of the corresponding carbonate anion. Use of at least an essentially stoichiometric amount of the base during the reaction with carbon dioxide provides the desired urethane and carbonate products.

The ammonium salt of the carbamate anion is prepared in solution in the presence of the base. The use of a base shifts the equilibrium toward the production of the carbamate anions. Where the reaction between the primary or secondary amine is carried out in the presence of a base, the reaction may be represented by the equation (1). The resulting ammonium carbamate salt solutions are normally homogeneous.

$$R_2R_3NH + Base + CO_2 = R_2R_3NCO^-_2\ HBase^+ \quad (1)$$

Equation (2) shows the results of the addition of the carbamate anion to a hydrocarbyl halide.

$$R_2R_3NCO_2^-\ HBase^+ + R_1\ Halide \quad (2)$$

$$R_2R_3NCO_2\!\!-\!\!R_1 + HBase^+\ Halide$$

In order to conduct the reaction with reasonable rates and commercially practicable yields, addition of the carbamate anion to the hydrocarbyl halide is performed in a polar aprotic solvent. Normally, the reaction, when conducted in a polar aprotic solvent, proceeds smoothly under mild conditions, e.g. at 25° C.–85° C. and 110 psi carbon dioxide pressure, to give the corresponding product in high yields.

Suitable primary or secondary amines used to prepare the carbamate esters in accordance with the present invention include amino acids such as glycine, aspartic acid and the like and amines represented by the following general formula:

$$R_2R_3NH$$

wherein $R_2$ and $R_3$ independently represent hydrogen, and alkyl, alkenyl, cycloalkyl, cycloalkenyl, aryl, aralkyl, aralkenyl, alkenaryl and alkaryl radicals having from 1 to about 22 carbon atoms, which radicals can be straight-chain or branched, provided that no more than one of $R_2$ and $R_3$ is hydrogen; and a radical represented by the formula $-(-R_5-)_n-NHR$ wherein R represents radicals as defined above for $R_2$, $R_5$ represents alkylene radicals having from about 1 to about 22 carbon atoms and n represents an integer of from 0 to about 8. Examples of $R_2$ and $R_3$ include methyl, ethyl, n-propyl, isopropyl, n-butyl, isobutyl, t-butyl, n-pentyl, isopentyl, n-hexyl, n-octyl, phenyl, benzyl, and the like. Specific examples of such suitable amines include N-ethyl(benzyl)amine, N,N-diallyamine; N,N-diethylamine; N-cyclohexylamine; N,N'-dimethylhexamethylene diamine and the like. In addition, $R_2$ and $R_3$ together with the nitrogen can be bound to form a saturated 5 to 9 membered ring radical. Examples of such ring radicals include morpholino, pyrrolidino, piperidino, and the like. Suitable amines also include polyamines such as, for example, tetraethylene pentamine, diethylene triamine, triethylene tetramine and pentaethylene hexamine and the like, as well as amino acids such as alanine, arginine, asparagine, aspartic acid, cysteine, glutamine glutamic acid, glycine, histidine, isoleucine, leucine, lysine, methionine, phenylalanine, proline, serine, threonine, tryptophan, tyrosine, valine, t-butyl glycine, ornithine, norleucine and the like, including $\beta$-amino acids and homo-$\beta$-amino acids.

The amine reacts with $CO_2$ to reversibly form the corresponding ammonium carbamate salt. To shift the equilibrium reaction more favorably to the ammonium carbamate salt, a base selected from the group consisting of a phosphazene compound and a mixture of a phosphazene compound and an organic, nitrogenous base selected from the group consisting of guanidine compounds, amidine compounds and mixtures thereof is added. Such phosphazene bases include t-butyliminotris(dimethylamino)phosphorane ($P_1$-tBu), 2-t-butylimino-2-diethylamino-1,3-dimethyl-perhydro-1,3,2-diazaphosphorane (BEMP), 1-t-butyl-4,4,4-tris(- dimethylamino)-2,2-bis-[tris(dimethylamino)phosphoranylideneamino]-2λ, 4λ-catenadi (phosphazene) (P4-tBu), and the like. Such organic, nitrogenous bases include amidines (e.g., DBU, 1,8-diazabicyclo[5.4.0]undec-7-ene, etc.) and guanidines (e.g., cyclohexyltetramethylguanidine, cyclohexyltetraethylguanidine, and the like).

The salt of the carbonate anion can be prepared in solution in the presence of a base selected from the group consisting of a phosphazene compound and a mixture of a phosphazene compound and an organic, nitrogenous base selected from the group consisting of guanidine compounds, amidine compounds and mixtures thereof. The reaction between the alcohol and carbon dioxide can be represented by the equation (3). The resulting carbonate salt solutions are normally homogeneous.

$$R_7R_8R_9COH + Base + CO_2 \rightleftharpoons R_7R_8R_9COCO_2^- H\text{-}Base^+ \quad (3)$$

Equation (4) shows the results of the addition of the complex of equation 3 to a hydrocarbyl halide.

$$R_7R_8R_9COCO_2^- \; HBase^+ R_4 \; Halide \quad (4)$$

$$R_7R_8R_9COCO_2 R_4 + HBase^+ \; Halide^-$$

Typically, the reaction, when conducted in a polar aprotic solvent, proceeds smoothly under mild conditions, e.g., at 25° C.–85° C. and 110 psi CO$_2$ pressure, to give the corresponding product in high yield.

Suitable primary, secondary and tertiary alcohols used to prepare the carbamate esters in accordance with the present invention can be represented by the following general formula:

$$R_7R_8R_9COH$$

R$_7$, R$_8$, and R$_9$ independently represent hydrogen, and alkyl, alkenyl, cycloalkyl, cycloalkenyl, aralkyl, aralkenyl, alkenaryl and alkaryl radicals having from 1 to about 22 carbon atoms, which radicals can be straight-chain or branched; a radical represented by the formula —(—R$_5$—)$_n$—OH wherein R$_5$ and n are as defined above; or when taken together along with C form an aromatic ring structure. Examples of R$_7$, R$_8$, and R$_9$ include methyl, ethyl, n-propyl, isopropyl, n-butyl, isobutyl, t-butyl, n-pentyl, isopentyl, n-hexyl, n-octyl, benzyl, and the like. Specific examples of suitable alcohols include benzyl alcohol, cyclohexanol, ethanol, n-butanol, isopropanol and the like. Suitable alcohols also include diols and polyols such as, for example, ethylene glycol, sorbitol, pentaerythritol and the like.

An advantage of the present process is that the reaction between the amine or the alcohol and CO$_2$ proceeds under mild temperature and pressure. Room temperature and a pressure of 110 psi CO$_2$ are suitable and are preferred. However, if desired, the reaction can be carried out between about 25° C. and about 150° C. under a CO$_2$ pressure in a range of from about 2 psi to about 400 psi, such as from about 10 psi to about 200 psi. A preferred temperature range is from about 30° C. to about 125° C., such as from about 35° C. to about 80° C.

Hydrocarbyl halides suitable for use in the present invention can be represented by the formula R$_1$X or XR$_1$X wherein R$_1$ represents alkyl, alkenyl, cycloalkyl, cycloalkenyl, aralkyl and aralkenyl radicals having from 1 to about 22 carbon atoms and X represents Cl, Br, I and F, preferably Cl. Examples of such hydrocarbyl halide include alkyl, cycloalkyl, alkenyl, aralkyl halides. Specific examples of such halides include methyl chloride, methyl iodide, ethyl bromide, n-butyl bromide, n-butyl chloride, iso-butyl chloride, amyl chloride, n-octyl chloride, benzyl bromide, benzyl chloride, (2-naphthyl)methyl chloride, 3-chlorocyclohexene, 3-chlorocyclohexane, 2-methyl allyl chloride, 4-chloro-2-butene and the like. Hydrocarbyl dihalides and polyhalides may also be used. For example, 1,4-dichloro-2-butene, 1,4-dichlorobutane, dichloro-p-xylene, and the like, may be utilized. The present invention is also applicable to formation of cyclic carbamates and carbonates wherein a suitable alcohol or amine, as described above, containing a suitable leaving group such as a halide is reacted with CO$_2$ as set forth herein, in the presence of a base selected from the group consisting of a phosphazene compound and a mixture of a phosphazene compound and an organic, nitrogenous base selected from the group consisting of guanidine compounds, amidine compounds and mixtures thereof.

The reaction between the salt and the hydrocarbyl halide is carried out in a suitable polar aprotic organic solvent. As utilized herein, the phrase "polar aprotic organic solvent" means an aprotic organic solvent having a dielectric constant of greater than about 10 ε as reported in Reichardt, C., "Solvents and Solvent Effects in Organic Chemistry," 2nd ed., VCH Verlagsgesellschaft, Weinheim, (1988), Table A-1, utilizing toluene (2.38ε) and tetrahydrofuran (7.58ε), both at 20° C., as standards. Other methods for determining dielectric constants are known and suitable solvents are those having a dielectric constant greater than that of tetrahydrofuran utilizing any of such methods. Examples of suitable solvents include acetonitrile, N-methyl pyrrolidone, dimethylformamide, dimethylsulfoxide, and the like, as well as mixtures thereof. Preferred solvents are acetonitrile and DMSO. Although not specifically required, it is preferred to utilize these same solvents to carry out the reaction between the amine or alcohol and carbon dioxide in order to avoid the step of isolating the salt. However, this reaction can also be conducted in other organic solvents which are not polar aprotic solvents, such as, for example, THF, methylene chloride and the like.

To obtain high selectivity for urethanes over amine products (oxygen vs. nitrogen attack) and high selectivity for carbonates over ethers, the anion is stabilized by the use of an essentially stoichiometric amount of a base selected from a phosphazene compound or a mixture of a phosphazene compound and an organic, nitrogenous base. The term base as utilized herein refers to a base utilized in addition to the reactant amine or alcohol. The phrase "organic, nitrogenous base" as used herein refers to a base other than the phosphazene compound which is utilized in addition to the reactant amine or alcohol. The phosphazene compounds of the invention are compounds represented by the formula:

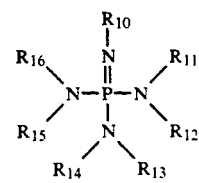

wherein $R_{10}$, $R_{11}$, $R_{12}$, $R_{13}$, $R_{14}$, $R_{15}$ and $R_{16}$ are selected from the group consisting of alkyl, aryl, alkaryl, aralkyl and cycloalkyl radicals having 1 to about 22 carbon atoms; or one of $R_{11}$ or $R_{12}$ together with one of $R_{13}$ or $R_{14}$, one of $R_{15}$ or $R_{16}$ together with one of $R_{13}$ or $R_{14}$, and $R_{10}$ together with one of $R_{11}$ or $R_{12}$ or one of $R_{15}$ or $R_{16}$ independently form a nitrogen-containing heterocycle; or $R_{11}$ together with $R_{12}$, $R_{13}$ together with $R_{14}$, and $R_{15}$ together with $R_{16}$ independently represent a radical represented by the formula:

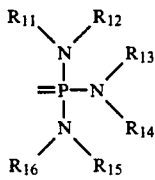

wherein $R_{11}$, $R_{12}$, $R_{13}$, $R_{14}$, $R_{15}$ and $R_{16}$ are as defined above.

Examples of phosphazene compounds which can be employed in the process of the invention include, but are not limited to, t-butyliminotris(dimethylamino)-phosphorane ($P_1$-tBu), 1-t-butyl-4,4,4 tris(dimethylamino)-2,2-bis-[tris(dimethylamino) phosphoranylideneamino]-2λ, 4λ-catenadi(phosphazene) ($P_4$-tBu), 2-t-butylimino-2-diethylamino-1,3-dimethyl-perhydro-1,3,2-diazaphosphorane (BEMP), t-butyliminotris(diethylamino)phosphorane, 2-t-octylimino-2-diethylamino-1,3-dimethyl-perhydro-1,3,2-diazaphosphorane, and the like, and mixtures of any two or more thereof.

The guanidine compounds of the invention are compounds represented by the formula:

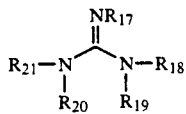

wherein $R_{17}$, $R_{18}$, $R_{19}$, $R_{20}$ and $R_{21}$ are independently selected from the group consisting of alkyl, aryl, alkaryl, aralkyl and cycloalkyl radicals having 1 to about 22 carbon atoms; or $R_{17}$ together with one of $R_{18}$, $R_{19}$, $R_{20}$ or $R_{21}$, $R_{18}$ and $R_{19}$, and $R_{20}$ and $R_{21}$ independently form a nitrogen-containing heterocycle.

The amidine compounds of the invention are compounds represented by the formula:

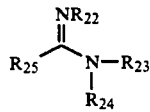

wherein $R_{22}$, $R_{23}$, $R_{24}$ and $R_{25}$ are independently selected from the group consisting of alkyl, aryl, alkaryl, aralkyl and cycloalkyl radicals having 1 to about 22 carbon atoms; or $R_{22}$ together with $R_{23}$ or $R_{24}$ and $R_{25}$ together with $R_{23}$ or $R_{24}$ independently form a nitrogen-containing heterocycle.

Examples of organic, nitrogenous bases which can be employed in the process of the invention include tetramethyl guanidine (TMG), cyclohexyltetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU) and the like, and mixtures of any two or more thereof. Addition of the pre-made carbamate, or carbonate, anion under carbon dioxide pressure to a solution of a hydrocarbyl halide in a suitable polar aprotic solvent gives high yields and selectivities of urethanes and carbonates and with high rates. The selection of the base in the formation of the carbamate or carbonate is important in order to obtain higher selectivities and thus higher yields.

Preferably, the molar ratio of base to the amine or alcohol starting materials will be within the range of from about 1:1 to about 10:1. A preferred molar ratio is in the range of from about 1:1 to about 1.5:1. A most preferred molar ratio is 1:1. The rate of reaction between the carbamate or carbonate salts and the hydrocarbyl halide can be increased by utilizing excess, up to about 2 moles per mole of carbamate or carbonate, hydrocarbyl halide. It is believed that use of such excess hydrocarbyl halide facilitates reaction conditions which are pseudo-first order as opposed to second order. Thus, in order to render the present process more commercially practicable, it is preferred to use an excess of such hydrocarbyl halide.

It is contemplated that mixtures of alcohols and mixtures of amines can be utilized effectively in the process of the present invention. Furthermore, it is contemplated that compounds which include both alcohol and amine functional groups, e.g., diethanolamine, can be utilized effectively in the process of the present invention. In addition, it is contemplated that an alcohol/amine mixture, e.g., a mixture of N-benzyl-N-ethyl amine and benzyl alcohol, can be utilized effectively in the process of the present invention. It is also contemplated that carbon disulfide can be utilized in place of carbon dioxide to produce the corresponding dithiocarbamates and dithiocarbonates.

Contemplated equivalents of the general formulas set forth above for the alcohols, amines and hydrocarbyl halides are compounds otherwise corresponding thereto and having the same general properties wherein one or more of the various R groups are simple variations of the substituents as defined therein, e.g., wherein R is a higher alkyl group or includes a substituent such as, for example, a halide, amino substituents, hydroxy substituents and the like. In addition, where a substituent is designated as, or can be, a hydrogen, the exact chemical nature of a substituent which is other than hydrogen at that position is not critical so long as it does not adversely affect the overall synthesis procedure. For example, where the above-specified alcohols and amines are mono- and difunctional alcohols and amines, equivalents thereof which are suitable for use in the present invention include polyols and polyamines. Where a halide is considered a leaving group, for example, as in the hydrocarbyl halide, other leaving groups such as tosyl, mesylate, triflate and the like, which are all well known in the art, are contemplated equivalents.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrated examples wherein parts and percentages are given on a molar basis unless otherwise specified.

EXAMPLES

All amines and alcohols used in the following examples were obtained either from Aldrich Chemical Company or Kodak Chemical Company and were used as received. Anhydrous solvents under nitrogen were purchased from Aldrich Chemical Co. P,-tBu(t-butyliminotris-(dimethylamino)-phosphorane) and BEMP(2-t-butylimino-2-diethylamino-1,3-dimethylperhydro-1,3,2-diazaphosphorane) were obtained from Fluka Chemical Corp. and used as received. Carbon dioxide was supplied either from Matheson (bone dry grade) or from Acetylene Gas Co. (welding grade) and used without any further purification.

Gas chromatographic analysis was performed on a Varian Model 3400 gas chromatograph with a model 8000 auto sampler using a 30 meter Megabore DB-1 (3μm) J & W Scientific column.

EXAMPLE 1

N,N-diethyl-benzyl carbamate: A Fischer-Porter bottle was charged with 0.73 g (10 mmol) diethyl amine, 2.34 g (10 mmol) $P_1$-tBu, 154 mg (1 mmol) biphenyl as an internal standard and 10 mL $CH_3CN$. This was attached to a pressure head and 40 psig carbon dioxide was added above the solution causing an exothermic reaction to occur. A second Fischer-Porter bottle was charged with 2.51 g (20 mmol) benzyl chloride and 10 mL $CH_3CN$ and to this was added 40 psig $CO_2$. After one hour the benzyl chloride solution was added all at once to the first Fischer-Porter bottle under 40 psig $CO_2$. The reaction mixture was heated to 40° C. and was monitored periodically by G.C. A maximum calculated yield of 28% of N,N-diethyl-benzyl carbamate was achieved after 2 h 15 min.

EXAMPLE 2

N,N-diethyl-benzyl carbamate: A Fischer-Porter bottle was charged with 0.73 g (10 mmol) diethyl amine, 2.74 g (10 mmol) BEMp, 154 mg (1 mmol) biphenyl as an internal standard and 10 mL $CH_3CN$. This was attached to a pressure head and 40 psig carbon dioxide was added above the solution causing an exothermic reaction to occur. A second Fischer-Porter bottle was charged with 2.51 g (20 mmol) benzyl chloride and 10 mL $CH_3CN$ and to this was added 40 psig $CO_2$. After one hour the benzyl chloride solution was added all at once to the first Fischer-Porter bottle under 40 psig $CO_2$. The reaction mixture was heated to 40° C. and was monitored periodically by G.C. A maximum calculated yield of 72% of N,N-diethyl-benzyl carbamate was achieved after 2 h.

EXAMPLE 3

N-Butyl benzyl carbamate: A Fischer-Porter bottle was charged with 1.46 g (20 mmol) n-butyl amine, 5.60 g (24 mmol) $P_2$-tBu, 308 mg (2 mmol) biphenyl as an internal standard and 10 mL $CH_3CN$. This was attached to a pressure head and 20 psig carbon dioxide was added above the solution causing an exothermic reaction to occur. A second Fischer-Porter bottle was charged with 5.06 g (40 mmol) benzyl chloride and 5 mL $CH_3CN$ and to this was added 20 psig $CO_2$. After one hour the benzyl chloride solution was added all at once to the first Fischer-Porter bottle under 20 psig $CO_2$. The reaction mixture was heated to 47° C. and was monitored periodically by G.C. A maximum calculated yield of 50% of N-butyl-benzyl carbamate was achieved after 24 h.

EXAMPLE 4

N-Butyl benzyl carbamate: A Fischer-Porter bottle was charged with 1.46 g (20 mmol) n-butyl amine, 6.55 g (24 mmol) BEMP, 308 mg (2 mmol) biphenyl as an internal standard and 20 mL $CH_3CN$. This was attached to a pressure head and 20 psig carbon dioxide was added above the solution causing an exothermic reaction to occur. A second Fischer-Porter bottle was charged with 5.06 g (40 mmol) benzyl chloride and 5 mL $CH_3CN$ and to this was added 20 psig $CO_2$. After one hour the benzyl chloride solution was added all at once to the first Fischer-Porter bottle under 20 psig $CO_2$. The reaction mixture was heated to 50° C. and was monitored periodically by G.C. A maximum calculated yield of 80.5% of N-butyl-benzyl carbamate was achieved after 19 h.

EXAMPLE 5

Butyl-benzyl carbonate: A Fischer-Porter bottle was charged with 0.74 g (10 mmol) n-butanol, 2.74 g (10 mmol) BEMP, 154 mg (1 mmol) biphenyl as an internal standard and 10 mL $CH_3CN$. This was attached to a pressure head and 40 psig carbon dioxide was added above the solution causing an exothermic reaction to occur. A second Fischer-Porter bottle was charged with 2.51 g (20 mmol) benzyl chloride and 10 mL $CH_3CN$ and to this was added 40 psig $CO_2$. After one hour the benzyl chloride solution was added all at once to the first Fischer-Porter bottle under 30 psig $CO_2$. The reaction mixture was heated to 55° C. and was monitored periodically by G.C. A maximum calculated yield of 76% of butyl-benzyl carbonate was achieved after 2 h.

EXAMPLE 6

This example illustrates the preparation of piperidinobenzyl carbamate using $P_1$-tBu as the base.

A Fischer-Porter bottle was charged with 0.85 g (10 mmol) piperidine, 2.34 g (10 mmol) $P_1$-tBu, 154 mg (1 mmol) biphenyl as an internal standard and 10 mL $CH_3CN$. This was attached to a pressure head and 40 psig carbon dioxide was added above the solution causing an exothermic reaction to occur. A second Fischer-Porter bottle was charged with 2.51 g (20 mmol) benzyl chloride and 5 mL $CH_3CN$ and to this was added 40 psig $CO_2$. After one hour the benzyl chloride solution was added all at once to the first Fischer-Porter bottle under 40 psig $CO_2$. The reaction mixture was heated to 44° C. and was the benzyl monitored periodically by G.C.. A maximum calculated yield of 25% of piperidino-benzyl carbamate was achieved after 4 h.

EXAMPLE 7

This example illustrates the preparation of piperidinobenzyl carbamate using BEMP as the base.

A Fischer-Porter bottle was charged with 0.85 g (10 mmol) piperidine, 2.74 g (10 mmol) BEMp, 154 mg (1 mmol) biphenyl as an internal standard and 10 mL $CH_3CN$. This was attached to a pressure head and 40 psig carbon dioxide was added above the solution causing an exothermic reaction to occur. A second Fischer-Porter bottle was charged with 2.51 g (20 mmol) benzyl chloride and 5 mL $CH_3CN$ and to this was added 40 psig $CO_2$. After one hour the benzyl chloride solution was added all at once to the first Fischer-Porter bottle under 40 psig $CO_2$. The reaction mixture was heated to 44° C. and was monitored periodically by G.C.. A maximum calculated yield of 52% of piperidino-benzyl carbamate was achieved after 20 h.

What is claimed is:

1. A process for preparing urethanes and carbonates comprising:
   (a) contacting $CO_2$ and a compound selected from the group consisting of an amine and an alcohol in the presence of a base selected from the group consisting of a phosphazene compound and a mixture of a phosphazene compound and an organic, nitrogenous base wherein said organic, nitrogenous base is selected from the group consisting of guanidine compounds, amidine compounds and mixtures thereof, under reaction conditions of time and temperature sufficient to produce an ammonium carbamate salt or carbonate salt corresponding to said amine or alcohol starting material, and
   (b) reacting, in a polar aprotic solvent, said salt with a primary or secondary hydrocarbyl halide under reaction conditions of time and temperature sufficient to produce the corresponding urethane or carbonate wherein said phosphazene compound is represented by the formula:

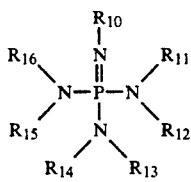

wherein $R_{10}$, $R_{11}$, $R_{12}$, $R_{13}$, $R_{14}$, $R_{15}$ and $R_{16}$ are independently selected from the group consisting of alkyl, aryl, alkaryl, aralkyl and cycloalkyl radicals; or one of $R_{11}$ or $R_{12}$ together with one of $R_{13}$ or $R_{14}$, one of $R_{15}$ or $R_{16}$ together with one of $R_{13}$ or $R_{14}$, and $R_{10}$ together with one of $R_{11}$ or $R_{12}$ or one of $R_{15}$ or $R_{16}$ independently form a nitrogen-containing heterocycle; or $R_{11}$ together with $R_{12}$, $R_{13}$ together with $R_{14}$, and $R_{15}$ together with $R_{16}$ independently represent a radical represented by the formula:

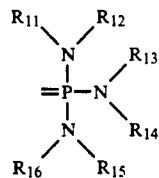

wherein $R_{11}$, $R_{12}$, $R_{13}$, $R_{14}$, $R_{15}$ and $R_{16}$ are as defined above.

2. The process of claim 1 wherein said polar aprotic solvent is selected from the group consisting of dimethylsulfoide, dimethylformamide, acetonitrile and N-methyl-2-pyrrolidone.

3. The process of claim 1 wherein said primary or secondary hydrocarbyl halide is represented by the formula $R_1X$ or $XR_1X$, wherein $R_1$ represents alkyl, cycloalkyl, cycloalkenyl, aralkyl and aralkenyl radicals having 1 to about 22 carbon atoms and X represents a halide.

4. The process of claim 3 wherein said X is chloride.

5. The process of claim 1 wherein said base is a phosphazene compound.

6. The process of claim 1 wherein said phosphazene compound is t-butyliminotris(dimethylamino) phosphorane or 2-t-butylimino-2-diethylamino-1,3-dimethylperhydro-1,3,2-diazaphosphorane.

7. The process of claim 1 wherein said amine is represented by the formula $R_2R_3NH$ or an amino acid, wherein $R_2$ and $R_3$ independently are hydrogen, radicals having 1 to about 22 carbon atoms selected from the group consisting of alkyl, alkenyl, cycloalkyl, cycloalkenyl, aryl, aralkyl, aralkenyl, alkaryl and alkenaryl, and radicals having the formula $-(-R_5-)_n-NHR$ wherein R represents hydrogen and radicals selected from the group consisting of alkyl, alkenyl, cycloalkyl, cycloalkenyl, aryl, aralkyl, aralkenyl, alkaryl and alkenaryl having 1 to about 22 carbon atoms, $R_5$ represents alkylene radicals having 1 to about 22 carbon atoms and n is an integer from 0 to about 8 provided that no more than one of $R_2$ and $R_3$ is hydrogen.

8. The process of claim 8 wherein said urethane is represented by the formula:

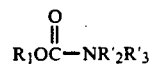

or

wherein $R_1$ represents alkyl, alkenyl, cycloalkyl, cycloalkenyl, aralkyl and aralkenyl radicals having 1 to about 22 carbon atoms provided that $R_1$ is not a tertiary radical of the formula $(R)_3C-$ or $(R)_2C=C(R)-$; $R_2'$ and $R_3'$ independently are hydrogen, radicals having 1 to about carbon atoms selected from the group consisting of alkyl, alkenyl, cycloalkyl, cycloalkenyl, aryl, aralkyl, aralkenyl, alkaryl and alkenaryl, and radicals having the formula:

wherein $R_1$ is as defined above, R represents hydrogen radicals having 1 to about 22 carbon atoms selected from the group consisting of alkyl, alkenyl, cycloalkyl, cycloalkenyl, aryl, aralkyl, aralkenyl, alkenaryl and alkaryl, $R_5$ represents alkylene radicals having 1 to about 22 carbon atoms and n is an integer from 0 to about 8, provided that no more than one of $R'_2$ and $R'_3$ is hydrogen; and $R''_3$ is hydrogen and radicals having 1 to about 22 carbon atoms selected from the group consisting of alkyl, alkenyl, cycloalkyl, cycloalkenyl, aryl, aralkyl, aralkenyl, alkenaryl and alkaryl.

9. The process of claim 1 wherein said amine is represented by the formula $R_2R_3NH$ wherein $R_2$ and $R_3$ together with the nitrogen form a saturated 5 to 9 membered ring radical.

10. The process of claim 9 where in said urethane is represented by the formula:

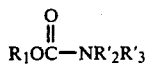

wherein $R'_2$ and $R'_3$ together with the nitrogen form a saturated 5 to 9 membered ring radical.

11. The process of claim 1 wherein said carbonate is represented by the formula:

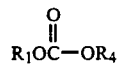

wherein $R_1$ represents alkyl, alkenyl, cycloalkyl, cycloalkenyl, aralkyl and aralkenyl radicals having 1 to about 22 carbon atoms provided that $R_1$ is not a tertiary radical of the formula $(R)_3C-$ or $(R)_2C=C(R)-$; and $R_4$ represents alkyl, alkenyl, cycloalkyl, cycloalkenyl, aralkyl, aralkenyl, alkenaryl and alkaryl radicals having 1 to about 22 carbon atoms and radicals represented by the formula:

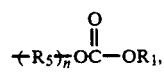

wherein $R_1$ is as defined above, $R_5$ represents alkylene radicals having 1 to about 22 carbon atoms, and n is an integer from 0 to about 8.

* * * * *

UNITED STATES PATENT AND TRADEMARK OFFICE
CERTIFICATE OF CORRECTION

PATENT NO. : 5,302,717
DATED : April 12, 1994
INVENTOR(S) : William D. McGhee and John J. Talley It is certified that error appears in the above-identified patent and that said Letters Patent is hereby corrected as shown below:

In col. 12, line 18, after "alkyl", insert --alkenyl--.

In col. 12, line 44, delete "Claim 8" and insert therefor --Claim 7--.

In col. 12, line 60, after "about" insert --22--.

In col. 13, line 2, before "radicals" insert --and--.

Signed and Sealed this

Fifteenth Day of November, 1994

Attest:

BRUCE LEHMAN

Attesting Officer

Commissioner of Patents and Trademarks